United States Patent [19]

Holmes et al.

[11] Patent Number: 4,826,993

[45] Date of Patent: May 2, 1989

[54] SUBSTITUTED DIAZOLIDINONES

[75] Inventors: Richard E. Holmes; Louis N. Jungheim, both of Indianapolis, Ind.

[73] Assignee: Eli Lilly and Company, Indianapolis, Ind.

[21] Appl. No.: 862,917

[22] Filed: May 14, 1986

Related U.S. Application Data

[63] Continuation-in-part of Ser. No. 728,734, Apr. 30, 1985, abandoned.

[30] Foreign Application Priority Data

Apr. 28, 1986 [EP] European Pat. Off. ........ 86303176.1

[51] Int. Cl.$^4$ ............................................. C07D 231/06
[52] U.S. Cl. .................................... 548/365; 546/211; 548/110; 548/115; 548/119; 548/364
[58] Field of Search ............... 548/364, 365, 110, 115, 548/119; 546/211

[56] References Cited

FOREIGN PATENT DOCUMENTS

| 64058 | 5/1968 | German Democratic Rep. ..................................... 548/365 |
| 110868 | 1/1975 | German Democratic Rep. ..................................... 548/365 |
| 1377596 | 12/1974 | United Kingdom ................ 548/365 |
| 1472052 | 4/1977 | United Kingdom ................ 548/364 |
| 2073740A | 10/1981 | United Kingdom ................ 548/365 |

OTHER PUBLICATIONS

Kochetkov et al., Zhurnal Obshchei Khimii, 31(10), pp. 3292–3298 (1961).
*Protective Groups in Organic Chemistry*, McOmie ed., 1973, pp. 43 and 46–55.
M. Ueda, M. Funayama and Y. Umai, *J. Polymer Science Polym. Chem. Ed.*, 15, pp. 1629–1635 (1977).
M. A. Breger, *Antibiotiki*, 16, pp. 26–27 (1961).
H. Dorn and A. Otto, *Angew. Chem. Int. Ed. Engl.*, 7, pp. 214–215 (1968).
H. Dorn and A. Otto, *Chem. Ber.*, 101, pp. 3287–3301 (1968).
H. Dorn and A. Zubek, *Z. Chem.*, 8, pp. 218–219 (1968).

*Primary Examiner*—Richard A. Schwartz
*Attorney, Agent, or Firm*—Paul C. Steinhardt; Leroy Whitaker

[57] ABSTRACT

4-Substituted 1-(optionally substituted)-diazolidinones are intermediates to 7-substituted bicyclic pyrazolidinone antimicrobials.

8 Claims, No Drawings

SUBSTITUTED DIAZOLIDINONES

CROSS-REFERENCE TO RELATED APPLICATION

This application is a continuation-in-part of L. N. Jungheim, U.S. patent application Ser. No. 728,734, filed Apr. 30, 1985, now abandoned.

SUMMARY OF THE INVENTION

This invention is directed to substituted diazolidinone compounds of the formula:

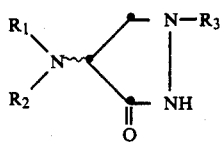

wherein $R_1$, $R_2$ and $R_3$ have the meanings defined below, and the acid addition salts thereof. The compounds are intermediates for 7-substituted bicyclic pyrazolidinone antimicrobials.

DETAILED DESCRIPTION OF THE INVENTION

The present invention embraces compounds of the Formula I:

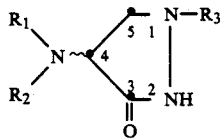

The ring system of the compound of Formula I is a 4-(substituted amino)-3-oxo-1-(optionally substituted)-1,2-diazolidine, which for brevity's sake will be referred to as a "diazolidinone" compound. In the above Formula I, the undulating line between position 4 of the diazolidinone ring and the protected amino group indicates that the instant diazolidinone compounds exist either as a mixture of varying proportions of enantiomers or as the pure 4-(R) or the pure 4-(S) enantiomer.

In the above Formula I, $R_1$ and $R_2$ are (a) taken together to form a phthalimido group; or (b) either $R_1$ or $R_2$ is hydrogen and the other of $R_1$ or $R_2$ is an amino-protecting group; or an acid-addition salt thereof.

$R_3$ in the above Formula I is either hydrogen or trifluoroacetyl.

The terms "amino-protecting group" and "protected amino" as used in the specification refer to substituents of the amino group commonly employed to block or protect the amino functionality while carrying out reactions at other functional groups on the compound. Examples of such amino protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcychexanyloxycarbonyl, 2-methylcyclohexanyloxycarbonyl, 2-(4-toluylslfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like, the benzoylmethylsulfonyl group, the 2-(nitro)-phenylsulfenyl group, the diphenylphosphine oxide group and like amino protecting groups. The species of amino-protecting group employed is not critical so long as the derivatized amino group is stable to the condition of subsequent reaction(s) on other positions of the diazolidinone molecule and can be removed at the appropriate point in the synthesis of 7-substituted bicyclic pyrazolidinone antimicrobials without disrupting the remainder of the molecule.

In particular, it is important not to subject the amino-substituted diazolidinone molecule (wherein $R_3$ is hydrogen) to strong nucleophilic bases or reductive conditions employing highly activated metal catalysts such as Raney nickel.

Preferred amino-protecting groups are the allyloxycarbonyl, the t-butoxycarbonyl and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

The term "acid addition salt" encompasses those salts formed by standard acid-base reactions with amino groups and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, d-10-camphorsulfonic, methanesulfonic, benzenesulfonic, para-toluenesulfonic, sorbic, picric, benzoic, cinnamic and like acids.

The compounds of Formula I also embrace the corresponding crystalline solvates. Thus, diazolidinones that crystallize with any number of (or any fraction thereof) of molecules of the mother liquor solvent are a part of the instant invention. The mother liquor solvent can be water or an organic solvent.

Examples of the compounds of Formula I include:
4-(R,S)-(t-butoxycarbonylamino)-3-oxo-1,2-diazolidine,
4-(S)-(t-butoxycarbonylamino)-3-oxo-1,2-diazolidine,
4-(R)-(t-butoxycarbonylamino)3-oxo-1,2-diazolidine,
4-(R,S)-(t-butoxycarbonylamino)-3-oxo-1,2-diazolidine p-toluenesulfonate salt,
4-(S)-(allyloxycarbonylamino)-3-oxo-1,2-diazolidine,
4-(S)-(tritylamino)-3-oxo-1,2-diazolidine, 4-(S)-(benzyloxycarbonylamino)-3-oxo-1,2-diazolidine,
4-(R,S)-(allyloxycarbonylamino)-3-oxo-1,2-diazolidine d-10-camphorsulfonate salt,
4-(R,S)-(tritylamino)-3-oxo-1,2-diazolidine,
4-(R,S)-(trichloroacetylamino)-3-oxo-1,2-diazolidine,
4-(R,S)-(benzolycarbonylamino)-3-oxo-1,2-diazolidine,
4-(R,S)-(chloroacetylamino)-3-oxo-1,2-diazolidine,
4-(R,S)-(4-methoxybenzyloxycarbonylamino)-3-oxo-1,2-diazolidine,
4-(R,S)-(cyclohexanoyloxycarbonylamino)-3-oxo-1,2-diazolidine,
4-(R,S)-(4-nitrobenzyloxycarbonylamino)-3-oxo-1,2-diazolidine,
4-(R,S)-(1,1-diphenylethoxycarbonylamino)-3-oxo-1,2-diazolidine,
4-(R,S)-(2-(methylsulfonyl)ethyloxycarbonylamino)-3-oxo-1,2-diazolidine,
4-(R,S)-(2-(trimethylsilyl)ethyloxycarbonylamino)-3-oxo-1,2-diazolidine,
4-(R,S)-(2,2,2-trichloroethoxycarbonylamino)-3-oxo-1,2-diazolidine,
4-(R,S)-(benzoylmethylsulfonylamino)-3-oxo-1,2-diazolidine,
4-(R,S)-(t-butoxycarbonylamino)-1-(trifluoroacetyl)-3-oxo-1,2-diazolidine,
4-(R,S)-(allyloxycarbonylamino)-1-(trifluoroacetyl)-3-oxo-1,2-diazolidine),
4-(R,S)-(trimethylsilylamino)-1-(trifluoroacetyl)-3-oxo-1,2-diazolidine),
4-(R,S)-(tritylamino)-1-trifluoroacetyl)-3-oxo-1,2-diazolidine,
4-(R,S)-benzyloxycarbonylamino)-3-oxo-1,2-diazolidine,
4-(R,S)-(trichloroacetylamino)-3-oxo-1,2-diazolidine,
4-(S)-(t-butoxycarbonylamino)-1-(trifluoroacetyl)-3-oxo-1,2-diazolidine,
4-(S)-(allyloxycarbonylamino)-1-(trifluoroacetyl)-3-oxo-1,2-diazolidine,
4-(S)-(trimethylsilylamino)-1-(trifluoroacetyl)-3-oxo-1,2-diazolidine, or
4-(S)-(tritylamino)-1-(trifluoroacetyl)-3-oxo-1,2-diazolidine;
or the p-toluenesulfonic acid addition salt of the above non-salt examples.

A preferred group of compounds of Formula I is the p-toluenesulfonic acid addition salt. A second preferred group of compounds of Formula I is when $R_1$ or $R_2$ is hydrogen and the other is t-butoxycarbonyl, and the corresponding p-toluenesulfonic acid addition salt.

A third preferred group of compounds occurs when the $C_4$ carbon of the diazolidinone ring is in the S configuration. Preferred compounds with the third preferred group have either $R_1$ or $R_2$ as hydrogen and the other as t-butoxycarbonyl.

The synthesis of enantiomeric mixtures of (1-unsubstituted) diazolidinones of Formula I is outlined below in Scheme I.

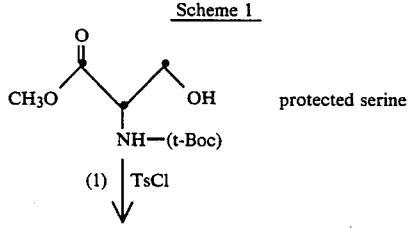

Scheme 1 protected serine

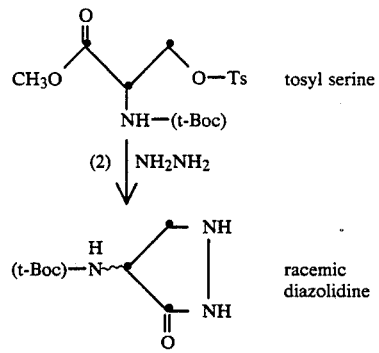

The above Scheme depicts the synthesis of 4-(t-butoxycarbonylamino) diazolidinone compounds. Diazolidinone compounds with different amino protecting groups are obtained from serine derivatized with an amino-protecting group other than t-butoxycarbonyl.

The first step in the synthesis of 1-(unsubstituted)-diazolidinones, represented by Reaction 1 in the above Scheme, is the tosylization of the hydroxy group of the protected serine derivative. The tosylization is carried out in methylene chloride with p-toluenesulfonyl chloride in the presence of a catalytic amount of 4-dimethylaminopyridine and greater than one equivalent of pyridine. The reaction mixture is stirred at room temperature overnight.

The tosylated serine obtained is reacted with 97% hydrazine to give enantiomeric mixtures of 1-(unsubstituted)diazolidinones, as depicted in Reaction 2. Reaction 2 should be carried in polar solvents such as chlorinated hydrocarbons, cyclic or acyclic ethers or $C_1$ to $C_4$ alcohols. A preferred group of solvents for the reaction is dichloromethane, methanol and chloroform, with dichloromethane being more preferred.

The temperature for Reaction 2 is not critical. It is preferred that the reaction be carried out between about room temperature to about the freezing temperature of the solvent. A more preferred temperature is approximately room temperature.

The reaction usually requires a period of about one to about forty-eight hours. The optimal reaction time can be determined by monitoring the progress of the reaction by conventional means such as chromatographic techniques (thin layer chromatography, high performance liquid chromatography, or column chromatography) and spectroscopic methods, alone or in conjuction with chromatographic techniques, such as infrared spectroscopy, nuclear magnetic resonance spectrometry and mass spectrometry. A preferred time period is from between about five to about sixteen hours.

The usual stoichiometry for Reaction 2 in the above Scheme 1 is a 4:1 ratio of hydrazine to tosyl serine reagent. Of course, a 1:1 ratio of reagents is permissible. It is preferred that the hydrazine reagent be present in excess, and especially preferred that the hydrazine be present in a 4:1 excess. Furthermore, the order of addition of either reagent is not critical.

The stereospecific synthesis of chiral diazolidinones of Formula I is diagrammed below in Scheme 2.

Scheme 2

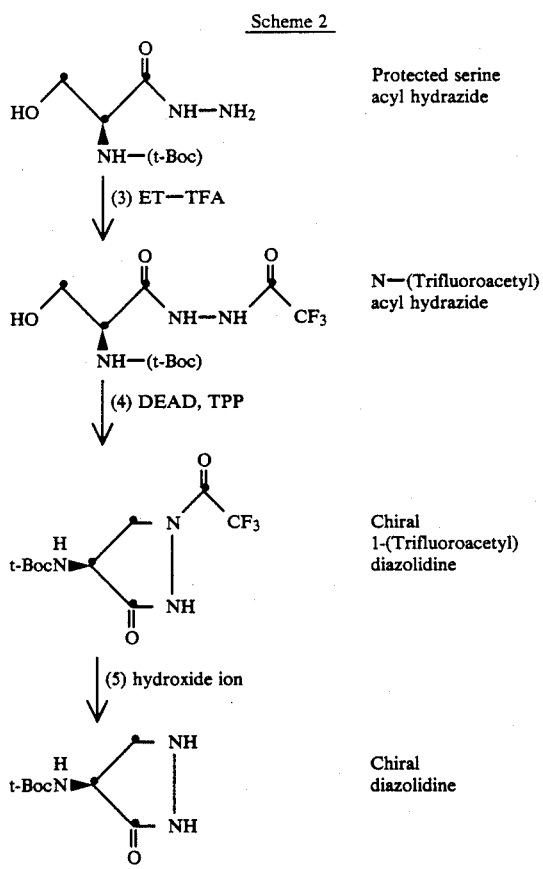

The above Scheme depicts the synthesis of 4-(S)-(t-butoxycarbonylamino)diazolidine compounds. Diazolidine compounds with the 4-(R) configuration are synthetized by starting with the protected D-serine acyl hydrazide instead of the L-isomer depicted above. Chiral diazolidines with amino-protecting groups other than t-butoxycarbonyl are synthesized a serine acyl hydrazide derivatized with an amino-protecting group other than t-butoxycarbonyl.

The protected serine acyl hydrazide precursor of Scheme 2 is synthesized in a procedure analogous to B. Iselin and R. Schwyzer, *Helv. Chim. Acta*, 44, p 169 (1961). The precursor is acylated with the trifluoroacetyl moiety, as set forth in Reaction 3 in the Scheme. The acylation is carried out in ethanol with an excess of ethylthio trifluorothioacetate ("ET-TFA"). The reaction mixture is stirred at room temperature for 65 hours.

The 1-(trifluoroacetyl)acyl hydrazide obtained from Reaction 3 is reacted with triphenylphosphine ("TPP") and diethyl azodicarboxylate ("DEAD"), as depicted above in Reaction 4. (Although the above Scheme depicts only the use of DEAD, the reaction will also proceed if either dimethyl azodicarboxylate or di(isopropyl)azodicarboxylate are substituted in the reaction.)

The stoichiometry of the process of Reaction 4 has the N-(trifluoroacetyl)acyl hydrazide, phosphine and diethyl azodicarboxylate reagent present in at least approximately a 1:1:1 molar ratio. The reaction will proceed in the presence of molar excesses above this ratio of any of the reagents or of the starting material.

The reaction is initiated by first combining (in any order) the solvent, the 1-(trifluoroacetyl)acyl hydrazide and the phosphine, and secondly adding the azodicarboxylate reagent.

The reaction temperature of Reaction 4 is a not critical parameter. The process can be carried out from approximately the freezing point to approximately the reflux temperature of the solvent. The preferred temperature is approximately room temperature.

The duration of Reaction 4 can be from approximately five minutes to approximately twenty four hours. The progress of the process can be monitored by standard methods (for example, thin layer chromatography, high performance liquid chromatography, etc.) The process is stopped when the monitoring method demonstrates that the reaction is substantially complete.

The solvents for Reaction 4 are aromatic hydrocarbon solvents such as benzene, toluene, xylenes, etc.; ethers such as diethyl ether, tetrahydrofuran, or 1,4-dioxane; chlorinated hydrocarbons such as methylene chloride, chloroform, carbon tetrachloride, dichloroethane, or chlorobenzene; amides such dimethylformamide and dimethylacetamide; and other solvents such as hexamethylphosphoramide. Tetrahydrofuran is the preferred solvent. It is also desirable, but not essential, to dry and deoxygenate the solvent before use in the process.

The chiral 1-(trifluoroacetyl)diazolidine obtained from Reaction 4 is deacylated with dilute sodium hydroxide solution to yield the chiral 1-(unsubstituted)-diazolidine. The deacylation reaction is represented as Reaction 5 in Scheme 2. The Reaction entails generally suspending the chiral 1-(trifluoroacetyl)diazolidine in water then adding at least two equivalents dilute aqueous sodium hydroxide solution. (For instance, a two-fold excess of 1M sodium hydroxide can be used. Preferably, sufficient sodium hydroxide solution is added to give the reaction solution an initial pH of from between about 11 to about 12). The resultant solution is stirred from about 10 minutes to about 3 hours at a temperature from about 10° C. to 25° C. When the reaction is substantially complete the reaction solution is neutralized by the addition of dilute acid, such as 1N hydrochloric acid.

The optimal reaction time for Reaction 5 can be determined by monitoring the progress of the reaction by conventional means such as chromatographic techniques (thin layer chromatography, high performance liquid chromatography, or column chromatography) and/or spectroscopic methods, such as infrared spectroscopy, nuclear magnetic resonance spectrometry and mass spectrometry. A preferred reaction time period is from between about 30 minutes to about 1.5 hours.

The diazolidinones of Formula I are intermediates to pyrazolidinium ylides of the Formula II:

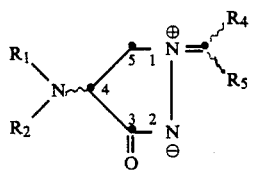

II

In the above Formula II,
$R_1$ and $R_2$ are
(1) taken together and form a phthalimido group; or
(2) either $R_1$ or $R_2$ is hydrogen and the other of $R_1$ or $R_2$ is an amino protecting group; and $R_4$ and $R_5$ are the same or different and are hydrogen, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl or a group of the formula

—COOR$_6$ wherein $R_6$ is $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, a carboxy protecting group, or a non-toxic, metabolically-labile ester-forming group.

The ylides of Formula II are synthesized by condensing a ketone or aldehyde with a 1-(unsubstituted)-diazolidine.

As a useful alternative procedure, the ketal of the ketone may be condensed with the diazolidine in the presence of an acid. For example, the diazolidine reagent is combined with acetone dimethyl acetal in methanol and then the solution is treated with d-10 camphorsulfonic acid. The mixture is refluxed for 1.5 hours to give the dimethyl ylide (i.e., $R_4$ and $R_5$ are methyl). The unsubstituted ylide (when $R_4$ and $R_5$ are hydrogen) is synthesized by combining the diazolidine reagent and 37% aqueous formaldehyde in methanol and stirring the mixture for between about twenty minutes to about 1.5 hours at room temperature. When $R_4$ and $R_5$ are different those skilled in the art will recognize that this final reaction will produce a mixture of E and Z isomers.

Chiral pyrazolidinium ylide intermediates (wherein $C_4$ is either in the (R) or (S) configuration) are synthetized from the corresponding chiral 1-(unsubstituted)-diazolidines of Formula I using the above-described conditions.

The synthesis of the above pyrazolidinium ylide intermediates are further described by L. N. Jungheim and R. E. Holmes, U.S. patent application No. 862,912, filed this even date, herein incorporated by reference, which in turn is a continuation-in-part of L. N. Jungheim, U.S. patent application No. 728,733, filed Apr. 30, 1985, herein incorporated by reference.

The ylides of Formula II are intermediates to 7-substituted bicyclic pyrazolidinone antimicrobials of Formula III

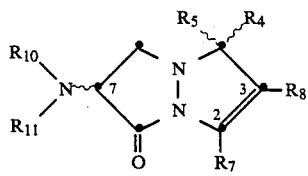

In Formula III, $R_4$ and $R_5$ include the substituents for $R_4$ and $R_5$ of the ylides of Formula II plus a carboxylic acid or a carboxylate salt. $R_{10}$ and $R_{11}$ of Formula III include all the substituents of the corresponding terms in Formula II plus substituents when either $R_{10}$ or $R_{11}$ is hydrogen and the other is an acyl group derived from a $C_1$ to $C_{30}$ carboxylic acid. (Examples of such acyl groups are the acyl groups bonded to the 6- and 7-amino groups of penicillins and cephalosporins, respectively). $R_7$ and $R_8$ in Formula III can be a variety of substituents, including a group of the formula

—COOR$_9$ wherein $R_9$ includes the substituents of the above $R_6$ plus, for example, hydrogen or an organic or inorganic cation. Further examples of substituents at $R_1$, $R_2$, $R_3$, $R_4$, $R_5$, $R_7$ and $R_8$ in Formula III can be found in L. N. Jungheim, S. K. Sigmund, C. J. Barnett, R. E. Holmes and R. J. Ternansky, U.S. patent application Ser. No. 862,906, filed this even date, herein incorporated by reference, which in turn is a continuation-in-part of L. N. Jungheim and S. K. Sigmund, U.S. patent application Ser. No. 729,021, filed Apr. 30, 1985, herein incorporated by reference.

The 7-substituted bicyclic pyrazolidinones of Formula III are synthesized, for example, by various 1,3-dipolar cycloaddition reactions with the ylides of Formula II. One method of cycloaddition reaction, (the addition of an ylide and a substituted acetylene) is represented below in Scheme 3:

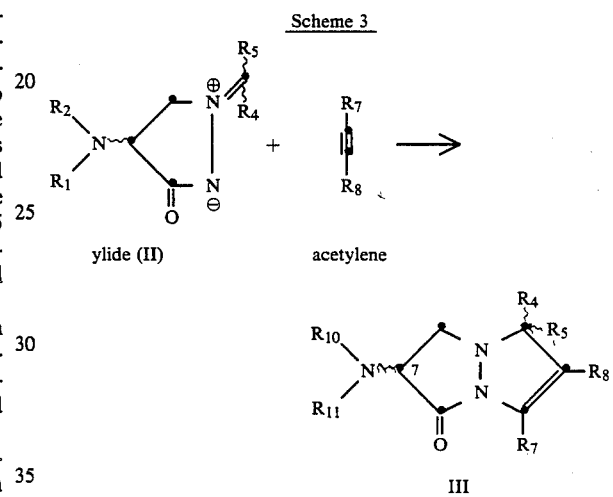

In the above Scheme 3, for brevity's sake, Formula III indicates only one of the two possible 2,3-regioisomer products of the reaction. The reaction represented by Scheme 3 can also produce the opposite 2,3-regioisomer as well as a mixture of the regioisomers.

In the above Scheme $R_1$, $R_2$, $R_4$ and $R_5$ are as defined above for Formula II, $R_7$ and $R_8$ are as defined for Formula III and either $R_{10}$ or $R_{11}$ is an amino protecting group and the other of $R_{10}$ or $R_{11}$ is hydrogen. When carrying out the reaction it is preferable to derivatize with protecting groups any of the acidic groups represented by $R_4$, $R_5$, $R_7$ or $R_8$. Examples of such acidic groups are the carboxylic acid group and the hydroxyimino group. It is especially preferred that any carboxylic acid groups be protected.

The reaction should be carried out in aprotic solvents. Examples of such solvents are the chlorinated hydrocarbons, the aromatic hydrocarbons and alkyl or aromatic cyano solvents. The preferred solvents for the above reaction are dichloromethane, acetonitrile, and 1,2-dichloroethane.

The temperature for the reaction is not critical. It is preferred that the reaction be carried out between about room temperature to about the reflux temperature of the solvent.

The reaction usually requires a period of about 1 to about 168 hours. The optimal reaction time can be determined by monitoring the progress of the reaction by conventional means such as chromatographic techniques (thin layer chromatography, high performance liquid chromatography, or column chromatography)

and spectroscopic methods (alone or in conjuction with chromatographic techniques), such as infrared spectroscopy, nuclear magnetic resonance spectrometry and mass spectrometry.

The usual stoichiometry for the reaction is a 1:1 ratio of ylide to acetylene reagent. Of course, an excess of either reagent is permissible. It is preferred that the acetylene reagent be present in excess, and especially preferred that the acetylene be present in a 2:1 excess. Furthermore, the order of addition of either reagent is not critical.

The regiospecificity of the cycloaddition in Scheme 2 is unpredictable. The stereochemical and electronic properties of the ylide and acetylene and the various reaction conditions have as yet yielded no clearly discernable regiospecific trends. Usually the reaction yields widely varying mixtures of 2,3-regioisomer products.

The stereospecificity of the cycloaddition of Scheme 3 at the $C_7$ position of the bicyclic pyrazolidinone product is determined by the stereochemistry at $C_4$ of the ylide starting material. Thus, if the ylide is chiral (either 4-(R) or 4-(S)) then the cycloaddition product will be chiral (7-(R) or 7-(S), respectively). Similarly, an $C_4$ enantiomeric mixture of ylide starting materials will yield a $C_7$ enantiomeric mixture of cycloaddition products.

The compounds produced by Scheme 3 above are the 7-(protected amino) derivatives of Formula III. In order to enhance the antimicrobial activity of the bicyclic pyrazolidinone compounds, it is desirable to replace the amino-protecting group with an acyl group derived from a $C_1$ to $C_{30}$ carboxylic acid. As discussed above, the acyl groups employed are typically those used to achieve the same purpose when bonded to the 6-amino group of a penicillin or a 7-amino group of a cephalosporin.

The first step for the acylation of a 7-(protected amino) bicyclic pyrazolidinone compound ("7-protected amino nucleus") is the removal of the amino protecting group. The conditions for the removal of these groups are well known in the cephalosporin and penicillin arts. For example, the trimethylsilyl protecting group is removed by simple hydrolysis, the t-butoxycarbonyl group is removed by acidic hydrolysis (either trifluoroacetic acid or a mixture of hydrochloric acid in glacial acetic acid), and the allyloxycarbonyl group is removed as a palladium complex.

Removal of the acid-labile amino protecting groups usually yields the 7-amino nucleus as a salt. The salt of the nucleus is neutralized by conventional procedures before acylation. For instance, the removal of the t-butoxycarbonyl group with trifluoroacetic acid leaves the trifluoroacetate salt of the resultant 7-amino compound. The salt is taken up in tetrahydrofuran and bis(-trimethylsilyl)trifluoroacetamide was added to yield the corresponding 7-amino compound. The (neutralized) 7-amino compound can be isolated then acylated or acylated in situ. Similarly, the removal of the t-butoxycarbonyl group with a mixture of hydrochloric acid in acetic acid leaves the hydrochloride salt. The hydrochloride salt is neutralized with a base such as N-methylmorpholine and generally acylated in situ.

The methods for the acylation of the 7-amino bicyclic pyrazolidinone compounds with the acyl side chain are similar to the methods for the acylation of 6-aminopenicillanic acid, 7-aminodesacetoxycephalosporanic acid and 7-aminocephalosporanic acid. One method is to simply combine the 7-amino nucleus with an acid chloride or acid bromide. The acid chloride or acid bromide may be formed in situ. Another method is to combine the 7-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di-(n-propyl)carbodiimide, N,N'-di-(iso-propyl)carbodiimide, N,N'-diallylcarbodiimide, N,N'-bis(p-dimethylaminophenyl)carbodiimide, N-ethyl-N'-(4''-ethylmorpholinyl)carbodiimide and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol may also be used. Dehydrating agents such as phosphorus oxychloride, alkoxyacetylenes and 2-halogenopyridinium salts (such as 2-chloropyridinium methyl iodide, 2-fluoropyridinium methyl iodide, and the like) may be used to couple the free acid or its acid salt with the 7-amino nucleus.

Another acylation method entails first converting the free carboxylic acid form (or the corresponding salt) of the acyl side chain to the active ester derivative which is in turn used to acylate the nucleus. The active ester derivative is formed by esterifying the free acid form with groups such as p-nitrophenol, 2,4-dinitrophenol, trichlorophenol, pentachlorophenol, N-chlorosuccinimide, N-chloro maleic imide, N-chlorophthalimide, 2-chloro-4,6-dimethoxytriazene, 1-hydroxy-1H-benzotriazole or 1-hydroxy-6-chloro-1H-benzotriazole. The active ester derivatives can also be mixed anhydrides, formed with groups such as methoxycarbonyl, ethoxycarbonyl, iso-butoxycarbonyl, trichloromethylcarbonyl, and iso-but-2-ylcarbonyl and the carboxylic acid of the side chain. The mixed anhydrides are synthesized by acylating the carboxylic acid of the acyl side chain.

Alternatively, the 7-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (e.g. tetrahydrofuran, acetonitrile, etc.). The resultant EEDQ derivative is used in situ to acylate the 7-amino nucleus.

Once the bicyclic pyrazolidinones are acylated with the appropriate acyl group derived from a $C_1$ to $C_{30}$ carboxylic acid, they are converted to the corresponding antimicrobial final product form by removing any remaining amino, hydroxy and/or carboxy protecting groups on the molecules. As discussed above, such removal methods are well known in the cephalosporin, penicillin and peptide arts. Once the carboxy groups are deprotected, the oral ester may be put on the desired carboxy group(s) at $R_4$, $R_5$, $R_7$ and $R_8$. The methods for making the oral ester derivatives are well known in the cephalosporin and penicillin art.

The antimicrobial compounds of Formula III inhibit the growth of certain organisms pathogenic to man and animals. The antimicrobial compounds are compounds wherein the various amino, hydroxy and/or carboxy protecting groups have been removed. The antimicrobial activity can be demonstrated in vitro using standard tube-dilution techniques. The in vitro tests demonstrate that the 7-(S) antimicrobial compounds are more active than either a mixture of corresponding $C_7$ enantiomers or the corresponding 7-(R) compounds. Representative pathogens which are sensitive to the antimicrobial compounds of Formula III include *Staphylococcus aureus*

$X1.1$, *Streptococcus pyogenes* C203, *Streptococcus pneumoniae* Park, *Hemophilus influenzae* 76 (ampicillin resistant), *Escherichia coli* N10, *Escherichia coli* EC14, *Escherichia coli* TEM (b-lactamase producer), *Klebsiella pneumoniae* X26, *Klebsiella pneumoniae* KAE ($\beta$-lactamase producer), *Klebsiella pneumoniae* X68, *Enterobacter aerogenes* C32, *Enterobacter aerogenes* EB17, *Enterobacter cloacae* EB5 (non-$\beta$-lactamase producer), *Salmonella typhi* X514, *Salmonella typhi* B35, *Serratia marcescens* X99, *Serratia marcescens* SE3, *Proteus morganii* PR15, *Proteus inconstans* PR33, *Providencia rettgeri* C24, *Citroboaeter freundii* CF17, and the like.

The antimicrobial compounds for which the diazolidinones of this invention are intermediates are useful for the therapeutic or prophylactic treatment of infections in warm-blooded animals caused by both gram-positive, gram-negative and acid-fast bacteria.

The antimicrobial compounds can be administered orally, parenterally (e.g. intravenously, intramuscularly or subcutaneously) or as a topical ointment or solution in treating bacterial infections of warm-blooded animals.

Further description of the synthesis and the properties of the bicyclic pyrazolidinones of Formula III are found in L. N. Jungheim, S. K. Sigmund, C. J. Barnett, R. E. Holmes and R. J. Ternansky, U.S. patent application Ser. No. 862,906, filed this even date which in turn is a continuation-in-part of L. N. Jungheim and S. K. Sigmund, U.S. patent application Ser. No. 729,021, filed Apr. 30, 1985, herein incorporated by reference.

The following Examples are provided to further illustrate the invention. It is not intended that the invention be limited in scope by reason of any of the following Preparations or Examples.

In the following Preparations and Examples, the terms melting point, nuclear magnetic resonance spectra, field desorption mass spectra, electron impact mass spectra, infra-red spectra, ultraviolet spectra, elemental analysis, high performance liquid chromatography and thin layer chromatography are abbreviated m.p., n.m.r., f.d.m.s., m.s., i.r., u.v., anal., HPLC and TLC, respectively. In addition, the adsorption maxima listed for the i.r. spectra are only those of interest and not all of the maxima observed.

The abbreviations THF, TFA and BSTFA stand for tetrahydrofuran, trifluoroacetate and N,O-bis(trimethylsilyl)trifluoroacetamide, respectively.

In conjunction with the n.m.r. spectra, the following abbreviations are used: "s" is singlet, "d" is doublet, "dd" is doublet of doublets, "t" is triplet, "q" is quartet, "m" is multiplet, "dm" is a doublet of multiplets and "br. s", "br. d" and "br. t" stand for broad singlet, doublet and triplet, respectively. "J" indicates the coupling constant in Hertz. "DMSO/$d_6$" is dimethyl sulfoxide where all protons have been replaced with deuterium.

The n.m.r. spectra were obtained on a Varian Associates EM-390 90 MHz, on a Jeol FX-90Q 90 MHz instrument, or on a General Electric QE-300 MHz instrument. The chemical shifts are expressed in $\delta$ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer Model 281 instrument. Ultraviolet Spectra were obtained on a Cary Model 118 instrument. Specific rotations were obtained on a Perkin-Elmer Model Q-41 instrument. Thin layer chromatography was carried out on E. Merck silica gel plates. Melting points reported are uncorrected.

EXPERIMENTAL SECTION

Preparation 1

Methyl 3-(p-Toluenesulfonate)-2-(S)-(t-Butoxycarbonylamino)Propionate

Methyl (3-hydroxy)-2-(S)-(t-butoxycarbonylamino)-propionate (58 g, 196 mmol), dry methylene chloride (150 ml), p-toluenesulfonyl chloride (43.35 g, 227.4 mmol), 4-(dimethylamino)pyridine (2.4 g, 19.6 mmol) and pyridine (30 ml, 371 mmol) were combined and stirred at room temperature overnight. The reaction solution was concentrated in vacuo to a pale yellow oil. The oil was stored in vacuo overnight, then the white solid that formed was isolated to give 75.33 g of crude product. The product was triturated in petroleum ether (approximately 200 ml) to yield methyl 3-(p-toluenesulfonate)-2-(S)-(t-butoxycarbonylamino)propionate:

n.m.r.: ($CDCl_3$, 90 MHz): $\delta$ 7.72, 7.31 (2x dd, 4, aromatic protons), 5.26 (m, 1, nitrogen proton), 4.48 (m, 1, C-2 proton), 4.32 (m, 2, C-3 protons), 3.68 (s, 3, methyl protons of methyl ester), 2.44 (s, 3, methyl protons of toluene moiety), 1.40 (s, 9, protons of t-butyl moiety); i.r. ($CHCl_3$): 3435, 3019, 1753, 1711, 1502, 1369, 1351, 1250, 1215, 1190, 1177 $cm^{-1}$; m.s.: 279, 210, 172, 91, 41;

Anal. Calcd. for $C_{16}H_{23}NO_7S$: Theory: C, 51.19; H, 6.71; N, 3.73; S, 8.54. Found: C, 51.05; H, 6.50; N, 3.63; S, 8.13.

EXAMPLE 1

4-(R,S)-(t-Butoxycarbonylamino)-3-Oxo-1,2-Diazolidine

Under a nitrogen atmosphere, dry methylene chloride (50 ml) was cooled in an ice bath and anhydrous hydrazine (11.0 g, 333 mmole), (97%) was added. The ice bath was removed and the solution was stirred until it warmed to room temperature. At this time a solution of methyl 3-(p-toluenesulfonate)-2-(S)-(t-butoxycarbonylamino)propionate (20.0 g, 53.6 mmole) in dry methylene chloride (50 ml) was gradually added. The reaction solution was stirred under nitrogen at room temperature for 5 hours. The solution was then concentrated under reduced pressure and the concentrate was taken up in saturated aqueous sodium bicarbonate solution. The aqueous solution was continuously extracted for 14 hours with methylene chloride (700 ml). The methylene chloride solution was dried over sodium sulfate, filtered and concentrated under reduced pressure to yield approximately 5.15 g, 48% of 4-(R,S)-(t-butoxycarbonylamino)-3-oxo-1,2-diazolidine: n.m.r. ($CDCl_3$, 90 MHz): $\delta$ 7.04 (m, 1), 5.12 (m, 1), 4.28 (m, 1, C-4 proton), 3.94 (m, 1, C-5 proton), 3.20 (m, 1, C-5 proton), 1.45 (s, 9, t-butyl protons); i.r. ($CHCl_3$): 3430, 3250, 3019, 2983, 1702, 1545, 1503, 1370, 1297, 1241, 1215, 1165 $cm^{-1}$; f.d.m.s.: $M^+ = 201$;

Anal. Calcd. for $C_8H_{15}N_3O_3$: Theory: C, 47.75; H, 7.51; N, 20.88. Found: C, 47.80; H, 7.56; N, 20.61.

EXAMPLE 2

4-(R,S)-(t-Butoxycarbonylamino)-3-Oxo-1,2-Diazolidine p-Toluenesulfonate Salt 4-(R,S)-(t-Butoxycarbonylamino)-3-oxo-1,2-diazolidine (1.7 g, 8.45 mmol) was slurried in methylene chloride (50 ml). p-Toluenesulfonic acid hydrate (1.6 g, 8.45 mmol) was added to the slurry. After 20 minutes the resultant solid material was collected then dried in vacuo for approximately 48 hours to yield 2.95 g of colorless 4-(R,S)-(t-butoxycarbonylamino)-3-oxo-1,2-diazolidine p-toluenesulfonate salt: n.m.r. (90 MHz, DMSO-d$_6$): δ 7.5 (d, 2, J=8), 7.1 (d, 2, J=8), 4.32 (m, 1), 3.9 (m, 1), 3.4 (m, 1) 2.3 (s, 3), 1.4 (s, 9); i.r. (KBr): 1742, 1704, 1537 cm$^{-1}$.

Preparation 2

4-(R,S)-(t-Butoxycarbonylamino)-3-Oxo-1-(Methylene)-1,2-Pyrazolidinium Ylide 4-(R,S)-t-(Butoxycarbonylamino)-3-oxo-1,2-diazolidine (4.02 g, 20 mmol) was dissolved in dry methanol (50 ml). 37% Aqueous formaldehyde (1.62 g, 20 mmol) was added, the mixture was stirred for 20 minutes at room temperature then concentrated in vacuo. The solvent was removed by azeotropic distillation with methanol in vacuo at 40° C. The resultant residue was dried in vacuo at 40° C. overnight to yield 4-(R,S)-(t-butoxycarbonylamino)-3-oxo-1-(methylene)-1,2-pyrazolidinium ylide: n.m.r. (90 MHz, CDCl$_3$): δ 6.1–5.3 (m, 2), 4.9–4.2 (m, 6), 4.0–3.6 (m, 2), 3.5–3.1 (m, 2), 1.4 (s, 18); i.r. (KBr): 3379, 2980, 2930, 1705, 1524, 1519, 1504, 1455, 1393, 1368, 1297, 1252, 1166 cm$^{-1}$; f.d.m.s.: M⊕=213.

Preparation 3

2,3-di(Allyl Carboxylate)-7-(R,S)-(t-Butoxycarbonylamino)-8-Oxo-1,5-Diazabicyclo[3.3.0]Octa-2-ene 4-(R,S)-(t-Butoxycarbonylamino)-3-oxo-1-(methylene)-1,2-pyrazolidiniumylide from Preparation 2 above was dissolved in dry acetonitrile (50 ml) and diallyl butynedioate (3.88 g, 20 mmol) was added. The mixture was heated to reflux for 3 hours then concentrated in vacuo. The resultant solid was chromatographed by HPLC on silica gel eluted with 2:1 hexane:ethyl acetate, to yield 2.67 g, 32.8% yield of 2,3-di(allyl carboxylate)-7-(R,S)-(t-butoxycarbonylamino)-8-oxo-1,5-diazabicyclo[3.3.0]octa-2-ene: n.m.r. (90 MHz, CDCl$_3$): δ 6.20–5.70 (m, 2, unsaturated protons on allyl groups), 5.52–5.0 (m, 5, C-7 proton and unsaturated protons in allyl group), 4.82 (dm, 2, J=6, unsaturated protons on allyl group on C-2 carboxylate), 4.64 (dm, 2, J=6, saturated protons on allyl group on C-3 carboxylate group), 4.38 (d, 1, J=13, C-4 proton), 4.04 (t, 1, J=8, C-6 proton), 3.92 (d, 1, J=13, C-4 proton), 2.88 (dd, 1, J=8, 12, C-6 proton), 1.45 (s, 9, protons of t-butyl group); u.v. (methanol): λ$_{max}$=345 (ε=8500); i.r. (CHCl$_3$): 3019, 1750, 1736, 1709, 1384, 1370, 1278, 1234, 1215, 1162 cm$^{-1}$;

Anal. Calcd. for C$_{19}$H$_{25}$O$_7$N$_3$: Theory: C, 56.01; H, 6.19; N, 10.31. Found: C, 56.24; H, 6.35; N, 10.10.

Preparation 4

2,3-di(Allyl Carboxylate)-7-(R,S)-[2-(Thien-2-yl)Acetamido]-8-Oxo-1,5-Diazabicyclo[3.3.0]Octa-2-ene A. Removal of Amino Protecting Group and Formation of TFA Salt 2,3-di(Allyl carboxylate)-7-(R,S)-(t-butoxycarbonylamino)-8-oxo-1,5-diazabicyclo[3.3.0]octa-2-ene (407 mg, 1 mmol) was dissolved in trifluoroacetic acid (2 ml) and the solution was stirred for 5 minutes then concentrated in vacuo.

B. Neutralization of TFA salt

The residue from Step A was taken up in THF (5 ml) and BSTFA (1.5 ml) was added while the mixture was being cooled to 0° C.

C. Acylation of Nucleus

A THF solution (1 ml) of 2-(thien-2-yl)acetyl chloride (176 mg, 1.1 mmol) was added to the solution from Step B and the resultant mixture was stirred at 0° C. for 20 minutes. The reaction mixture was then poured into ethyl acetate and the resulting organic mixture was washed with saturated sodium bicarbonate solution, 0.2N hydrochloric acid, brine, dried over magnesium sulfate and filtered. The filtrate was concentrated in vacuo to give 700 mg of crude oily residue. The residue was chromatographed on a silica gel preparatory-scale TLC plate eluted with 1:1 hexane:ethyl acetate solution to give 270 mg, 62% yield of 2,3-di(allyl carboxylate)-7-(R,S)-[2-(thien-2-yl)acetamido]-8-oxo-1,5-diazabicyclo[3.3.0]octa-2-ene: n.m.r. (90 MHz, CDCl$_3$): δ 7.22 (m, 1, C-5 proton of thienyl group), 6.96 (m, 2, C-3 and C-4 protons of thienyl group), 6.56 (br. d, 1, J=6, amido proton), 6.20–5.60 (m, 2, C-2 proton of allyl groups), 5.60–5.10 (m, 4, C-3 (unsaturated) protons of allyl groups), 5.0 (m, 1, C-7 proton), 4.80 (dm, 2, J=6, C-1 protons of allyl group on C-2 carboxylate group), 4.64 (dm, 2, J=6, C-1 protons on allyl group on C-3 carboxylate group), 4.36 (d, 1, J=12, C-4 proton), 4.08 (t, 1, J=8, C-6 proton), 3.92 (d, 1, J=12, C-4 proton), 3.80 (s, 2, methylene protons of acetamido group), 2.86 (dd, 1, J=8, 12, C-6 proton); u.v. (methanol): λ$_{max}$=340 (ε=6850), 230 (ε=12,500); m.s.: M⊕=431; i.r. (CHCl$_3$) 1750, 1705 cm$^{-1}$;

Anal. Calcd. for C$_{20}$H$_{22}$N$_3$O$_6$S: Theory: C, 55.68; H, 4.91; N, 9.74; S, 7.43. Found: C, 55.97; H, 5.21; N, 9.52; S, 7.23.

Preparation 5

2,3-di(Carboxylic Acid)-7-(R,S)-[2-(Thien-2-yl)Acetamido]-8-Oxo-1,5-Diazabicyclo[3.3.0]Octa-2-ene Triphenylphosphine (35 mg, 0.13 mmol) was added to a solution of palladium(II) acetate (6 mg, 0.026 mmol) in acetone (3 ml). The mixture was stirred until a white precipitate formed (10 minutes). An acetone solution (3 ml) of 2,3-di(allyl carboxylate)-7-(S)-[2-(thien-2-yl)acetamido]-8-oxo-1,5-diazabicyclo[3.3.0]octa-2-ene (200 mg, 0.46 mmol) was added to the mixture. After the resultant mixture became homogenous, it was cooled to 0° C. and tri(n-butyl)tin hydride (0.27 ml, 1 mmol) was added. The solution was stirred at 0° C. for 30 minutes. 1N Hydrochloric acid (1 ml) was added and the solution was stirred for an additional 10 minutes. The solution was filtered, diluted with water (30 ml), then extracted with hexane (4 X, 50 ml). The aqueous phase was separated and freeze-dried to give 170 mg of yellow powder. The powder was triturated with ethyl acetate, sonicated, centrifuged, and the recovered solid was dried in vacuo to give 2,3-di(carboxylic acid)-7-(R,S)-[2-(thien-2-yl)acetamido]-8-oxo-1,5-diazabicyclo[3.3.0]octa-2-ene: n.m.r. (90 MHz, acetone-d$_6$) δ 7.20 (m, 1, C-5 proton of thienyl group), 6.94 (m, 2, C-3 and C-4 protons of thienyl group), 5.2–4.6 (m, 2, acetamido nitrogen proton and C-7 proton), 4.24 (d, 1, J=13, C-4 proton), 4.0–3.8 (m, 2, side chain methylene proton), 3.80 (s, 2, a C-6 proton and a C-4 proton), 3.0 (dd, 1, J=8, 12, a C-6 proton); u.v. (methanol): λ$_{max}$=345 (ε=4000), 226 (ε=7000); f.d.m.s.: (M+1)$^+$=352; i.r. (KBr): 1730, 1699, 1533, 1438, 1405, 1377, 1338, 1246, 1209, 1188 cm$^{-1}$.

Preparation 6

N-(t-Butoxycarbonyl) (L)-Serine Trifluoroacetyl Acyl Hydrazide

N-(t-Butoxycarbonyl) (L)-serine acyl hydrazide (32.85 g, 150 mmol) was suspended in ethanol (400 ml). Ethylthio trifluorothioacetate (30 ml, 37.02 g, 234.3 mmol) was added to the suspension and the resultant mixture was stirred at room temperature for 65 hours. The solvent was removed in vacuo and the residue was dissolved in diethyl ether (160 ml). A seed crystal was added to the diethyl ether solution and the resultant crystals were collected by filtration (approx. 27 g). The filtrate was evaporated in vacuo and diethyl ether (50 ml) was added to the residue. The solids that formed on standing were removed by filtration to yield approximately 16.5 g of additional product. The two batches of solids collected by filtration were combined and recrystallized from diethyl ether (3 liters). After effecting solution, the solution was reduced to approximately 450 ml to yield (after a second crop) 41.04 g, 87% yield of N-(t-butoxycarbonyl) (L)-serine trifluoroacetyl acyl hyrdrazide: n.m.r. (300 MHz, DMSO-d$_6$): δ 11.5 (br. s, 1), 10.33 (s, 1), 6.84 (d, 1, J=9), 4.9 (t, 1, J=7, (OH)), 4.1 (m, 1), 3.59 (br. m, 2), 1.4 (s, 9); specific rotation: $[\alpha]_D^{25} = -25.87°$ (10.05 mg/ml in methanol); m.p. 143°-144° C. (first crop), 142°-144° C. (second crop).

Anal. Calcd. for C$_{10}$H$_{16}$N$_3$O$_5$F$_3$: Theory: C, 38.10; H, 5.12; N, 13.33; Found: C, 38.34; H, 4.89; N, 13.16.

EXAMPLE 3

4-(S)-(t-Butoxycarbonylamino)-1-(Trifluoroacetyl)-3-Oxo-1,2-Diazolidine

N-(t-Butoxycarbonyl) (L)-serine trifluoroacetyl acyl hydrazide (3.78 g, 12 mmol) and triphenylphosphine (3.46 g, 13.2 mmol) were dissolved in THF (50 ml). To the solution was added a THF solution (10 ml) of 95% diethyl azodicarboxylate (2.42 g, 2.19 ml, 13.2 mmol). The resultant mixture was stirred at room temperature for six hours and then the solvent was removed in vacuo. The residue was dissolved in ethyl acetate (100 ml) and then the solution was washed with aqueous sodium bicarbonate solution (33 ml, 3X). The sodium bicarbonate extracts were combined, aqueous saturated brine solution (70 ml) was added and the resultant mixture was extracted with ethyl acetate (120 ml, 3X). The sodium bicarbonate solution was then layered with additional ethyl acetate (200 ml) and 1N hydrochloric acid (approx. 80 ml) was added until the sodium bicarbonate solution had a pH of 2.5. The ethyl acetate layer was separated and the aqueous layer was extracted with additional ethyl acetate (4X, 125 ml). The ethyl acetate extracts were combined, washed with saturated aqueous brine (125 ml, 2X), dried over sodium sulfate, filtered, and taken to dryness in vacuo. The resultant residue was dissolved in acetonitrile (100 ml) then the acetonitrile was removed in vacuo. Treatment of the residue with acetonitrile was repeated to yield 3.06 g, 96% yield of 4-(S)-(t-butoxycarbonylamino)-1-(trifluoroacetyl)-3-oxo-1,2-diazolidine: n.m.r. (300 MHz, CDCl$_3$): δ 5.25 (d, 1, J=6), 4.81 (t, 1), m 4.6 (m, 1), 4.06 (t, 1), 1.46 (s, 9); i.r. (CHCl$_3$): 1722, 1682, 1518 cm$^{-1}$; (f.d.m.s.) (m/e): M$^+$=297; specific rotation: $[\alpha]_D^{25} = -88.14°$ (10.03 mg/ml in methanol);

Anal. Calcd for C$_{10}$H$_{14}$N$_3$O$_4$F$_3$: Theory: C, 40.41; H, 4.75; N, 14.14. Found: C, 40.58; H, 5.01; N, 13.92.

EXAMPLE 4

4-(S)-(t-Butoxycarbonylamino)-3-Oxo-1,2-Diazolidine 4-(S)-(t-butoxycarbonylamino)-1-(trifluoroacetyl)-3-oxo-1,2-diazolidine (2.97 g, 10 mmol) was suspended in water (30 ml), 1N sodium hydroxide solution (20 ml, 0.8 g, 20 mmol) was added to raise the pH of the solution to 12.2 and the resultant mixture was stirred for one hour at room temperature. The pH of the mixture was adjusted to 7.2 by the addition of 1N hydrochloric acid (10 ml). Sodium chloride (13 g) was added to the solution and the mixture was extracted with chloroform (50 ml, 8X). The chloroform extracts were combined, washed with saturated aqueous sodium chloride solution (75 ml), dried over sodium sulfate, filtered, and evaporated to dryness in vacuo. Diethyl ether (100 ml) was added to the residue and then the ether was removed in vacuo to yield 0.798 g of a white solid of 4-(S)-(t-butoxycarbonylamino)-3-oxo-1,2-diazolidine: n.m.r. (300 MHz, DMSO-d$_6$): δ 9.23 (s, 1), 7.04 (d, 1, J=9), 5.24 (br. s, 1,), 4.24 (m, 1), 3.41 (t, 1), 2.88 (t, 1), 1.38 (s, 9); specific rotation: $[\alpha]_D^{25} = -74.16°$ (10.06 mg/ml in methanol); (the compound was dried overnight at 80° C. before analysis):

Anal. Calcd. for C$_8$H$_{15}$N$_3$O$_3$: Theory: C, 47.75; H, 7.51; N, 20.88. Found: C, 47.75; H, 7.46; N, 20.62.

Procedure 8

2-(Allyl Carboxylate)-3-(Methyl Carboxylate)-7-(S)-(t-Butoxycarbonylamino)-8-Oxo-1,5-Diazabicyclo-[3.3.0]Octa-2-ene

Step 1

Formation of Pyrazolidinium Ylide 4-(S)-(t-butoxycarbonylamino)-3-oxo-1,2-diazolidine (20.1 g, 100 mmol) was suspended in 1,2-dichloroethane (400 ml), 37% aqueous formaldehyde solution (8.51 ml, 3.15 g, 105 mmol) was added and the resultant mixture was stirred at room temperature for 1.5 hours.

Step 2

Cycloaddition of Acetylene

Allyl methyl butynedioate (18.48 g, 110 mmol) was added to the mixture from Step 1 and the resultant mixture was refluxed for 6.5 hours. The volume of the reaction mixture was reduced by half in a flask fitted with a Dean-Stark trap. Hexane (200 ml) was added and the mixture was allowed to stand until an oil formed. The solvent was decanted, the oil was dissolved in ethyl acetate (300 ml) and the solution was taken to dryness in vacuo to yield 17.3 g of a foam. The foam was chromatographed using preparatory-scale high performance liquid chromatography using a silica column eluted with a gradient of 0 to 40% ethyl acetate in isooctane (8 liters). The product-containing fractions were combined to yield 1.456 g of a yellow solid. The solid was recrystallized from a mixture of ethyl acetate and hexane to yield 0.55 g of 2-(allyl carboxylate)-3-(methyl carboxylate)-7-(S)-(t-butoxycarbonylamino)-8-oxo-1,5-diazabicyclo[3.3.0]octa-2-ene: n.m.r. (300 MHz, CDCl$_3$): δ 6.00 (m, 1), 5.38 (m, 2), 5.1 (br. d, J=6), 4.86 (d, 2), 4.74 (m, 1), 4.37 (d, 1, J=13), 4.08 (t, 1), 3.91 (d, 1, J=13), 3.77 (s, 3), 2.86 (t, 1), 1.46 (s, 9); i.r. (KBr): 1751, 1710, 1687 cm$^{-1}$; u.v. (ethanol): $\lambda_{max}$=346 ($\epsilon_{max}$=8489); f.d.m.s. (m/e): M$^+$=381; specific rotation: $[\alpha]_D^{25} = -481.92°$ (10.01 mg/ml in methanol); m.p. 111°–113° C.;

Anal. Calcd for $C_{17}H_{23}N_3O_7$: Theory: C, 53.54; H, 6.08; N, 11.02. Found: C, 53.83; H, 6.06; N, 10.77

Procedure 9

2-(Allyl Carboxylate)-3-(Methyl Carboxylate)-7-(S)-Amino-8-Oxo-1,5-Diazabicyclo[3.3.0]Octa-2-ene Hydrochloride Salt 2-(Allyl carboxylate)-3-(methyl carboxylate)-7-(S)-(t-butoxycarbonylamino)-8-oxo-1,5-diazabicyclo[3.3.0]octa-2-ene (0.1905 g, 0.5 mmol) was added to 3M hydrochloric acid in glacial acetic acid (7 ml) and the resultant mixture was stirred at room temperature for five minutes then taken to dryness in vacuo. The resultant yellow solid was dissolved in methylene chloride (20 ml) and the mixture was sonicated and evaporated in vacuo. The methylene chloride/sonication procedure was repeated two more times. The solid was dried in vacuo for 1.5 hours to yield to 2-(allyl carboxylate)-3-(methyl carboxylate)-7-(S)-amino-8-oxo-1,5-diazabicyclo[3.3.0]octa-2-ene hydrochloride salt.

Procedure 10

2-(Allyl Carboxylate)-3-(Methyl Carboxylate)-7-(S)-[2-(2-(Allyloxycarbonylamino)Thiazol-4-yl-2-(Z)-(Methoxyiminoacetamido)]-8-Oxo-1,5-Diazabicyclo[3.3.0]Octa-2-ene Under a nitrogen atmosphere, 2-[2-(N-allyloxycarbonylamino)thiazolo-4-yl]-2-(Z)-methoxyiminoacetic acid (0.1425 g, 0.5 mmol) was suspended in dried methylene chloride (5 ml). The suspension was cooled to 0° C. then 6-chloro-2,4-dimethoxy-1,3,5-triazine (0.088 g, 0.5 mmol) and N-methylmorpholine (0.0505 g, 0.5 mmol) were added. The resultant solution was stirred at 0° C. for forty minutes. Additional N-methylmorpholine (0.0505 g, 0.5 mmol) and then a methylene chloride suspension (5 ml) of 2-(allyl carboxy)-3-(methyl carboxylate)-7-(S)-amino-8-oxo-1,5-diazabicyclo[3.3.0]octa-2-ene hydrochloride salt (0.5 mmol) were added. After all the solid dissolved, the solution was stirred at room temperature for 20 hours then evaporated to dryness in vacuo. The residue was dissolved in ethyl acetate (70 ml) and water (15 ml), the layers were separated, and the ethyl acetate was extracted sequentially with 0.1N hydrochloric acid (10 ml, 3X), saturated aqueous sodium bicarbonate solution (20 ml, 3X), brine solution (20 ml, 3X), dried over sodium sulfate, filtered, and evaporated to dryness in vacuo to yield 280 mg of a yellow solid. The solid was recrystallized from a mixture of methylene chloride and di(isopropyl) ether to yield 136 mg of the 2-(allyl carboxylate)-3-(methyl carboxylate)-7-(S)-[2-(2-(allyloxycarbonylamino)thiazol-4-yl)-2-(Z)-methoxyiminoacetamido)]-8-oxo-1,5-diazabicyclo[3.3.0]octa-2-ene: n.m.r. (300 MHz, DMSO-d$_6$): δ 12.1 (s, 1), 9.32 (d, 1, J=9), 7.43 (s, 1), 5.94 (m, 2), 5.34 (m, 4), 5.09 (m, 1), 4.83 (d, 2, J=6), 4.7 (d, 2, J=6), 4.31 (d, 1, J=13), 4.02 (d, 1, J=13), 3.88 (overlapping t and s, 4), 3.69 (s, 3), 3.18 (t, 1); u.v. (ethanol); λ$_{max}$=342 (ε$_{max}$=8680), 264 (13,626), 209 (25,137); f.d.m.s. (m/e): M$^+$=548, 490; specific rotation: $[\alpha]_D^{25} = -351.45°$ (10.01 mg/ml in methanol).

Anal. Calcd for $C_{22}H_{24}N_6O_9S$: Theory: C, 48.17; H, 4.41; N, 15.32. Found: C, 48.09; H, 4.41; N, 15.02.

Procedure 11

2-(Carboxylic Acid)-3-(Methyl Carboxylate)-7-[2-(2-Aminothiazol-4-yl)-2-(Z)-Methoxyiminoacetamido]-8-Oxo-1,5-Diazabicyclo[3.3.0]Octa-2-ene Hydrate Palladium(II) acetate (18 mg, 0.08 mmol) was suspended in acetone (4 ml). Triphenylphosphine (105 mg, 0.4 mmol) was washed into the suspension with additional acetone (2 ml) and the resultant mixture was stirred at room temperature for 20 minutes. 2-(Allyl carboxylate)-3-(methyl carboxylate)-7-[2-(2-(allyloxycarbonylamino)thiazol-4-yl)-2-(Z)-methoxyiminoacetimido]-8-oxo-1,5-diazabicyclo[3.3.0]octa-2-ene (0.497 g, 0.9096 mmol) was suspended in a mixture of acetone (45 ml) and acetonitrile (15 ml) was then added to the reaction suspension. The suspension was stirred at room temperture for 35 minutes then cooled to 0° C. Tri(nbutyl)tin hydride (0.548 g, 1.81 mmol, 0.506 ml) was slowly added to the cooled suspension and the mixture was stirred at 0° C. for 30 minutes then at room temperature for 50 minutes. The mixture was cooled to 0° C. then 1N hydrochloric acid (1.82 ml, 1.81 mmol) was added. The resultant mixture was stirred at 0° C. for 10 minutes then at room temperature for 5 minutes. The mixture was filtered, water (130 ml) was added to the filtrate, and the resultant mixture was filtered through a pad of Celite TM. The filtrate was extracted with hexane (4X, 40 ml), and the aqueous layer was filtered through a pad of Celite TM then reduced in vacuo to about 75% volume. The resultant yellow solid was recovered by filtration through a pad of Celite TM and the filtrate was extracted with ether (2X, 75 ml), concentrated in vacuo to remove any residual ether and the resultant yellow solution was lyophilized. The lyophilized solid was dissolved in water (75 ml), filtered and chromatographed on a preparatory-scale high performance liquid chromatograph using a C$_{18}$ reverse phase column eluted with a gradient of 0 to 10% methanol/0.5% acetic acid/water (8 liters) then a gradient of 10 to 25% methanol/0.5% acetic acid/water (8 liters) to yield 91.5 mg of 2-(carboxylic acid)-3-(methyl carboxylate)-7-[2-(2-aminothiazol-4-yl)-2-(Z)-methoxyiminoacetamido]-8-oxo-1,5-diazabicyclo[3.3.0]octa-2-ene: n.m.r. (300 MHz, DMSO-d$_6$): δ 9.18 (d, 1, J=10), 7.24 (br. s, 2), 6.94 (s, 1), 5.02 (m, 1), 4.23 (d, 1, J=13), 3.9 (d, 1, J=13), 3.8 (overlapping t and s, 4), 3.1 (t, 1); i.r. (KBr): 1726, 1688, 1670.5 cm$^{-1}$; u.v. (ethanol): λ$_{max}$=328 (ε$_{max}$=10,950), 233 (16,013); f.d.m.s. (m/e): M$^+$=425; specific rotation: $[\alpha]_D^{25} = -326.35°$ (9.83 mg/ml in methanol).

Anal. Calcd for $C_{15}H_{16}N_6O_7S\cdot H_2O$: Theory: C, 40.72; H, 4.10; N, 19.00 Found: C, 40.81; H, 3.70; N, 19.03.

We claim:
1. A compound of the formula

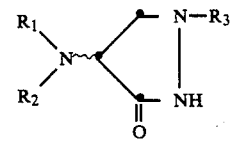

wherein:
R$_1$ and R$_2$ are
(a) taken together to form a phthalimido group; or
(b) either R$_1$ or R$_2$ is hydrogen and the other of R$_1$ or R$_2$ is t-butoxycarbonyl formyl, trityl, phthalimido, trichloroacetyl, chloroacetyl, bromoacetyl, idoacetyl, benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarobnyl, 3-bromobenzyloxycarbonyl, 4-nitrobenzylxoycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanloxycarbonyl, 1-methylcyhexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, benzoylmethylsulfonyl, 2-(nitro)-phenylsulfenyl, or the diphenylphosphine oxide group; or an acid-addition salt thereof; and $R_3$ is hydrogen or trifluoroacetyl.

2. A compound of claim 1, wherein either $R_1$ or $R_2$ is hydrogen and the other is t-butoxycarbonyl.

3. A compound of claim 1, wherein the compound is a p-toluenesulfonic acid addition salt.

4. A compound of claim 2, wherein the compound is a p-toluenesulfonic acid addition salt.

5. A compound of claim 1 of the formula

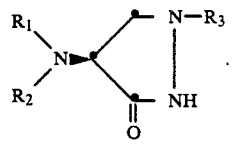

6. A compound of claim 5, wherein either $R_1$ or $R_2$ is hydrogen and the other is t-butoxycarbonyl.

7. A compound of claim 6, wherein $R_3$ is hydrogen.

8. A compound of claim 6, wherein $R_3$ is trifluoroacetyl.

* * * * *